United States Patent
Wang et al.

(10) Patent No.: US 11,580,410 B2
(45) Date of Patent: Feb. 14, 2023

(54) 3-D CONVOLUTIONAL AUTOENCODER FOR LOW-DOSE CT VIA TRANSFER LEARNING FROM A 2-D TRAINED NETWORK

(71) Applicant: RENSSELAER POLYTECHNIC INSTITUTE, Troy, NY (US)

(72) Inventors: Ge Wang, Loudonville, NY (US); Hongming Shan, Troy, NY (US); Wenxiang Cong, Albany, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 95 days.

(21) Appl. No.: 16/964,388

(22) PCT Filed: Jan. 24, 2019

(86) PCT No.: PCT/US2019/014895
§ 371 (c)(1),
(2) Date: Jul. 23, 2020

(87) PCT Pub. No.: WO2019/147767
PCT Pub. Date: Aug. 1, 2019

(65) Prior Publication Data
US 2020/0349449 A1    Nov. 5, 2020

Related U.S. Application Data

(60) Provisional application No. 62/795,829, filed on Jan. 23, 2019, provisional application No. 62/621,114, filed on Jan. 24, 2018.

(51) Int. Cl.
*G06T 5/00*   (2006.01)
*G06T 5/50*   (2006.01)
(Continued)

(52) U.S. Cl.
CPC .......... *G06N 3/088* (2013.01); *G06N 3/0454* (2013.01); *G06T 5/002* (2013.01); *G06T 5/50* (2013.01);
(Continued)

(58) Field of Classification Search
None
See application file for complete search history.

(56) References Cited

U.S. PATENT DOCUMENTS

2015/0201895 A1    7/2015  Suzuki
2017/0132512 A1*   5/2017  Ioffe ................... G06K 9/6256
(Continued)

OTHER PUBLICATIONS

Li, "Bottleneck Supervised U-Net for Pixel-wise Liver and Tumor Segmentation", arXiv:1810.10331v1, https://doi.org/10.48550/arXiv.1810.10331 (Year: 2018).*
(Continued)

*Primary Examiner* — Jiangeng Sun
(74) *Attorney, Agent, or Firm* — Murtha Cullina LLP; Anthony P. Gangemi

(57) ABSTRACT

A 3-D convolutional autoencoder for low-dose CT via transfer learning from a 2-D trained network is described, A machine learning method for low dose computed tomography (LDCT) image correction is provided. The method includes training, by a training circuitry, a neural network (NN) based, at least in part, on two-dimensional (2-D) training data. The 2-D training data includes a plurality of 2-D training image pairs. Each 2-D image pair includes one training input image and one corresponding target output image. The training includes adjusting at least one of a plurality of 2-D weights based, at least in part, on an objective function. The method further includes refining, by the training circuitry, the NN based, at least in part, on three-dimensional (3-D) training data. The 3-D training data includes a plurality of 3-D training image pairs. Each 3-D
(Continued)

training image pair includes a plurality of adjacent 2-D training input images and at least one corresponding target output image. The refining includes adjusting at least one of a plurality of 3-D weights based, at least in part, on the plurality of 2-D weights and based, at least in part, on the objective function. The plurality of 2-D weights includes the at least one adjusted 2-D weight.

15 Claims, 7 Drawing Sheets

(51) Int. Cl.
  *G06N 3/088*  (2023.01)
  *G06N 3/04*  (2023.01)

(52) U.S. Cl.
  CPC *G06T 2200/04* (2013.01); *G06T 2207/10081* (2013.01); *G06T 2207/20081* (2013.01); *G06T 2207/20084* (2013.01)

(56) References Cited

U.S. PATENT DOCUMENTS

| | | | |
|---|---|---|---|
| 2018/0218502 A1* | 8/2018 | Golden | G06N 3/08 |
| 2019/0080456 A1* | 3/2019 | Song | G06T 7/11 |
| 2019/0105009 A1* | 4/2019 | Siemionow | A61B 6/542 |
| 2019/0130578 A1* | 5/2019 | Gulsun | G06N 3/0445 |
| 2019/0164288 A1* | 5/2019 | Wang | G06T 5/002 |
| 2019/0325621 A1* | 10/2019 | Wang | G06N 3/0472 |
| 2020/0311914 A1* | 10/2020 | Zaharchuk | G06T 7/0012 |

OTHER PUBLICATIONS

International Search Report and The Written Opinion of the International Searching Authority, International Application No. PCT/US2019/014895, dated Apr. 15, 2019.

Yang, W., et al., "Low-dose CT Image Postprocessing Based on Residual Convolutional Network," IEEE Access, pp. 1-9, Oct. 2017.

Badretale, S., et al., "Fully Convolutional Architecture for Low-Dose CT Image Noise Reduction," IOP Conference Series: Materials Science and Engineering, pp. 1-6, 2017.

\* cited by examiner

3-D CONVOLUTIONAL AUTOENCODER FOR LOW-DOSE CT VIA TRANSFER LEARNING FROM A 2-D TRAINED NETWORK

CROSS REFERENCE TO RELATED APPLICATION(S)

This application claims the benefit of U.S. Provisional Application No. 62/621,114, filed Jan. 24, 2018, and U.S. Provisional Application No. 62/795,829, filed Jan. 23, 2019, which are incorporated by reference as if disclosed herein in their entireties.

FIELD

The present disclosure relates to a three-dimensional (3-D) autoencoder for low-dose computed tomography (CT), in particular to, a 3-D convolutional autoencoder for low-dose CT via transfer learning from a two-dimensional (2-D) trained network.

BACKGROUND

Computed tomography (CT), utilizing x-ray radiation to create internal images of the body, is a widely used imaging modality in clinical, industrial and other applications. The widespread use of CT has raised public concern that, while CT helps a large number of patients, additional cancer cases may be induced by CT-related x-ray radiation. Although CT provides a benefit in noninvasive imaging, such as for cancer screening, decreasing the radiation dose is desirable. However, reducing the radiation dose may increase noise and/or artifacts in reconstructed CT images. Such noise and/or artifacts may adversely affect diagnostic performance.

SUMMARY

In some embodiments, a machine learning method for low dose computed tomography (LDCT) image correction is provided. The method includes training, by a training circuitry, a neural network (NN) based, at least in part, on two-dimensional (2-D) training data. The 2-D training data includes a plurality of 2-D training image pairs. Each 2-D image pair includes one training input image and one corresponding target output image. The training includes adjusting at least one of a plurality of 2-D weights based, at least in part, on an objective function.

The method further includes refining, by the training circuitry, the NN based, at least in part, on three-dimensional (3-D) training data. The 3-D training data includes a plurality of 3-D training image pairs, Each 3-D training image pair includes a plurality of adjacent 2-D training input images and at least one corresponding target output image. The refining includes adjusting at least one of a plurality of 3-D weights based, at least in part, on the plurality of 2-D weights and based, at least in part, on the objective function. The plurality of 2-D weights includes the at least one adjusted 2-D weight.

In some embodiments of the method, the NN corresponds to a generator network of a Wasserstein generative adversarial network (WGAN) with gradient penalty. In some embodiments of the method, the objective function includes an adversarial loss function and a perceptual loss function.

In some embodiments of the method, each 3-D training image pair includes three adjacent 2-D training input images. In some embodiments of the method, the NN includes a convolutional neural network.

In some embodiments, the method further includes correcting, by the trained NN, an actual LDCT image to approximate a corresponding actual normal dose CT (NDCT) image, the correcting including at least one of noise reduction and/or artifact reduction.

In some embodiments of the method, the NN is a contracting path-based convolutional auto encoder (CPCA) including a plurality of main convolutional layers, a plurality of deconvolutional layers and a plurality of contracting paths, each contracting path coupled between an output of a respective convolutional layer and a respective selected deconvolutional layer. In these embodiments of the method, each of the plurality of contracting paths includes a respective contracting convolutional layer. In some embodiments of the method, each weight is selected from the group including a filter parameter and a network parameter.

In some embodiments, a neural network (NN) is provided. The NN includes a contracting path-based convolutional auto encoder (CPCA). The CPCA includes a plurality of main convolutional layers coupled in series, a plurality of deconvolutional layers coupled in series and a plurality of contracting paths. Each contracting path is coupled between an output of a respective convolutional layer and a respective selected deconvolutional layer. The CPCA is trained based, at least in part, on two-dimensional (2-D) training data. The 2-D training data includes a plurality of 2-D training image pairs. Each 2-D image pair includes one training input image and one corresponding target output image. The training includes adjusting at least one of a plurality of 2-D weights based, at least in part, on an objective function. The CPCA is refined based, at least in part, on three-dimensional (3-D) training data. The 3-D training data includes a plurality of 3-D training image pairs. Each 3-D training image pair includes a plurality of adjacent 2-D training input images and at least one corresponding target output image. The refining includes adjusting at least one of a plurality of 3-D weights based, at least in part, on the plurality of 2-D weights and based, at least in part, on the objective function. The plurality of 2-D weights includes the at least one adjusted 2-D weight.

In some embodiments of the NN, the CPCA corresponds to a generator network of a Wasserstein generative adversarial network (WGAN) with gradient penalty. In some embodiments of the NN, the objective function includes an adversarial loss function and a perceptual loss function. In some embodiments of the NN, the CPCA is configured to correct an actual low dose computed tomography (LDCT) image to approximate a corresponding actual normal dose computed tomography (NDCT) image, the correcting including at least one of noise reduction and/or artifact reduction.

In some embodiments of the NN, each of the plurality of contracting paths includes a respective contracting convolutional layer. In some embodiments of the NN, at least one of the NN includes a convolutional neural network and/or each weight is selected from the group including a filter parameter and a network parameter.

In some embodiments of the NN, the CPCA includes a first main convolutional layer, a second main convolutional layer, a third main convolutional layer and a fourth main convolutional layer; a first deconvolutional layer, a second deconvolutional layer, a third deconvolutional layer and a fourth deconvolutional layer; and a first contracting path coupling an output of the first main convolutional layer to the fourth deconvolutional layer, a second contracting path coupling an output of the second main convolutional layer to the third deconvolutional layer, and a third contracting path coupling an output of the third main convolutional layer to the second deconvolutional layer.

In some embodiments of the NN, the NN further includes a plurality of rectified linear units (ReLUs), each ReLU coupled an output of a respective main convolutional layer or an output of a respective deconvolutional layer.

In some embodiments a low dose computed tomography (LDCT) image correction system is provided. The LDCT image correction system includes at least one device arranged to perform any embodiments of the method.

In some embodiments a low dose computed tomography (LDCT) image correction device is provided. The LDCT image correction device includes means to perform any embodiments of the method.

In some embodiments a computer readable storage device is provided. The device has stored thereon instructions that when executed by one or more processors result in the following operations including any embodiments of the method.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

Figure 1:
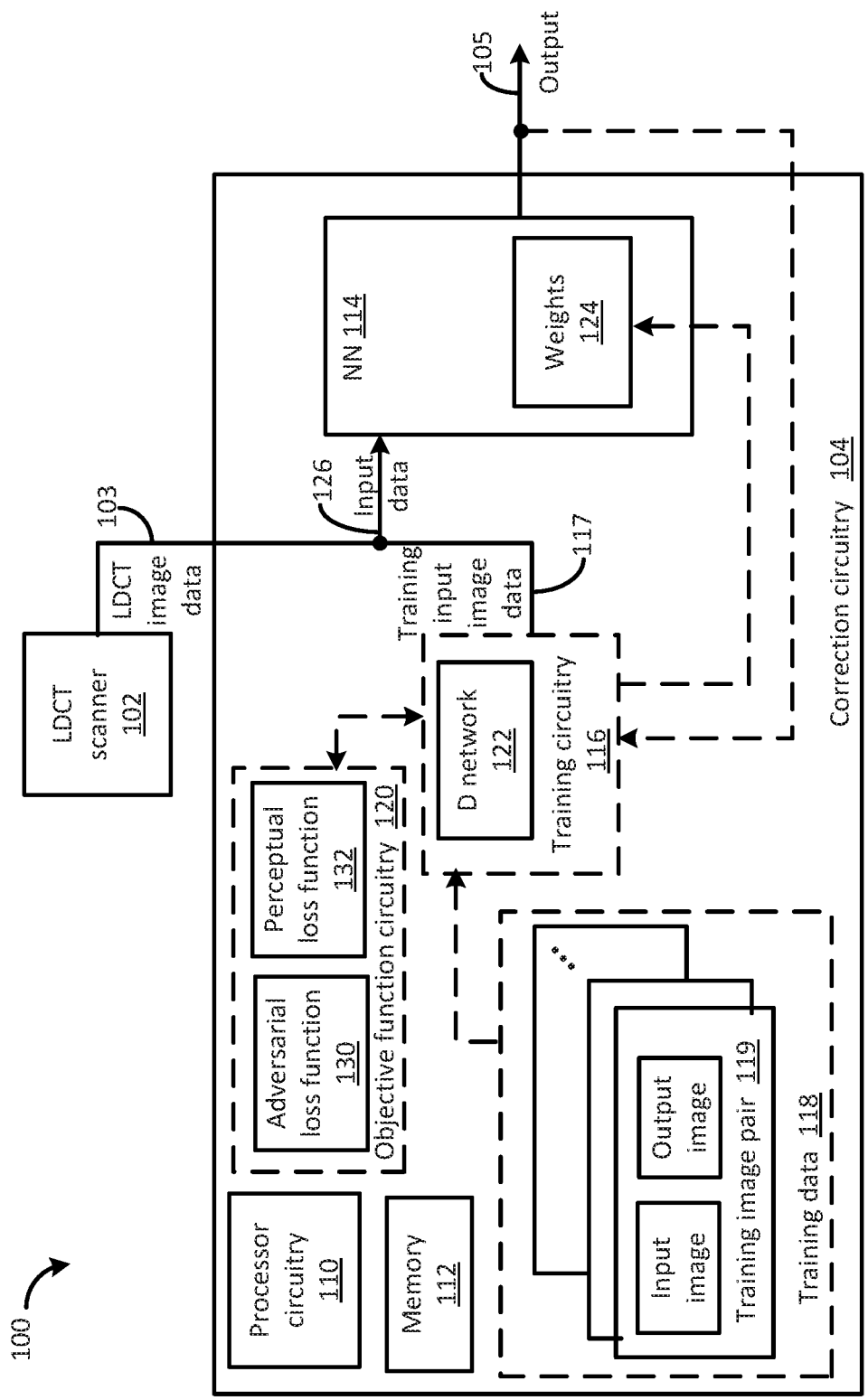
FIG. 1 illustrates a functional block diagram of a system including a neural network (NN) consistent with several embodiments of the present disclosure.

Generally, the present disclosure relates to a low-dose computed tomography (LDCT) image correction system. The LDCT image correction system corresponds to a 3-D convolutional autoencoder for low dose CT via transfer learning from a 2-D trained network. The LDCT image correction system is configured to reduce noise and/or artifacts that may be present in an LDCT image, to approximate a corresponding normal dose computed tomography (NDCT) image. The LDCT image correction system includes a neural network (NN). In one nonlimiting example, the NN may include a convolutional neural network. The NN may be trained based, at least in part, on reconstructed CT images and based, at least in part, on an objective function. During training, the NN may correspond to a generator network of a generative adversarial network (GAN). For example, the GAN may correspond to a Wasserstein GAN (WGAN) with gradient penalty. In another example, the objective function may include both an adversarial loss function and a perceptual loss function.

A method, system and/or apparatus is configured to train the NN using 2-D CT image data. The training includes determining 2-D weights to optimize the objective function. As used herein, "weights" may include filter parameters and/or network parameters. The method, system and/or apparatus is then configured to fine tune (i.e., refine) the NN using 3-D image data and based, at least in part, on the 2-D weights. The method, system and/or apparatus is configured to correct LDCT images that have been reconstructed based, at least in part, on raw sinograms, thus, the correcting corresponds to post-processing. Training the NN using 2-D image data and refining based, at least in part, on the 2-D weights is generally less computationally expensive than training from scratch using 3-D image data.

In an embodiment, a method for LDCT image correction may include training, by a training circuitry, a NN based, at least in part, on two-dimensional (2-D) training data. The 2-D training data includes 2-D images. The 2-D training data may include a plurality of 2-D training image pairs. Each 2-D image pair may include one training input image and one corresponding target output image. The training may include adjusting at least one of a plurality of 2-D weights based, at least in part, on an objective function. In an embodiment, the objective function may include an adversarial loss function and a perceptual loss function.

The method may further include refining, by the training circuitry, the NN based, at least in part, on the three-dimensional (3-D) training data. The 3-D training data may include a plurality of 3-D training image pairs. Each 3-D training image pair may include a plurality of adjacent 2-D training input images and at least one corresponding target output image. The refining may include adjusting at least one of a plurality of 3-D weights based, at least in part, on the plurality of 2-D weights and based, at least in part, on the objective function. The plurality of 2-D weights may include the at least one adjusted 2-D weight.

In an embodiment, the NN may correspond to a contracting path-based convolutional autoencoder (CPCA) that includes a plurality of main convolutional layers, a plurality of deconvolutional layers and a plurality of contracting paths. Each contracting path may be coupled between an output of a respective convolutional layer and a respective selected deconvolutional layer. Each contracting path may be configured to receive a respective feature map from the corresponding main convolutional layer and to provide a representation of the feature map to the selected deconvolutional layer.

FIG. 1 illustrates a functional block diagram of a system 100 including a neural network (NN) consistent with several embodiments of the present disclosure. System 100 includes an LDCT scanner 102 and correction circuitry 104. During normal operation, LDCT scanner 102 is configured to provide low-dose x-ray radiation to an object to be imaged (not shown), to capture resulting attenuated x-ray radiation (i.e., sinogram) and to reconstruct a corresponding LDCT image based, at least in part, on the sinogram. The reconstructed LDCT image may include noise and/or an artifact that may not be present in a corresponding normal dose CT (NDCT) image.

Correction circuitry 104 includes processor circuitry 110, memory 112 and NN 114. Correction circuitry 104 may further include training circuitry 116, training data 118 and objective function circuitry 120. In one nonlimiting example, NN 114 may include and/or correspond to a convolutional neural network. In another nonlimiting example, NN 114 may correspond to and/or include a contracting path-based convolutional autoencoder (CPCA). As used herein, CPCA corresponds to a conveying path-based encoder decoder (CPCE). Training circuitry 116 is configured to acquire training data 118 and to manage training NN 114, as described herein. Training data 118 includes a plurality of training image pairs, e.g., training image pair 119. Each training image pair includes a training input image and a corresponding target output image. Each target output image may be relatively high quality. Relatively high quality corresponds to an NDCT image with limited or no noise and/or artifacts present. Each training input image is a 2-D LDCT image (i.e., "slice") and each corresponding target output image is a 2-D NDCT image that corresponds to the two-dimensional LDCT image.

Processor circuitry 110 may include, but is not limited to, a single core processing unit, a multicore processor, a graphics processing unit, a microcontroller, an application-specific integrated circuit (ASIC), a field programmable gate array (FPGA), a programmable logic device (PLD), etc. Processor circuitry 110 may be configured to perform one or more operations of NN 114, training circuitry 116 and/or objective function circuitry 120. Memory 112 may be configured to store training data 118 and/or information and/or data associated with operation of NN 114 and/or training circuitry 116.

NN 114 may include weights 124. The weights may be generated and/or adjusted during training of NN 114, as will be described in more detail below. NN 114 is configured to receive input data 126 and to provide output 105. During normal operation, input data 126 corresponds to LDCT image data 103 received from LDCT scanner 102. LDCT image data 103 may include a plurality of adjacent two-dimensional LDCT images ("slices"). In one nonlimiting example, LDCT image data 103 provided to NN 114 may include three adjacent LDCT slices.

Objective function circuitry 120 corresponds to an objective function and may include an adversarial loss function 130 and/or a perceptual loss function 132. Objective function circuitry 120 may be configured to include objective function parameters related to evaluation and/or optimization of the corresponding objective function.

During training, input data 126 corresponds to training input image data 117. In one nonlimiting example, the training input image data 117 may include one training 2-D input image. In another nonlimiting example, the training input image data 117 may include a plurality (e.g., 3 or 9) of adjacent training 2-D input images. During training, training circuitry 116 is configured to acquire a plurality of training image pairs, e.g., training image pair 119, and to provide the corresponding input image(s) to NN 114 as training input image data 117. Training input image data 117 may be 2-D or 3-D. 2-D input image data corresponds to one 2-D CT image and 3-D input image corresponds to a plurality of adjacent 2-D CT images. In one nonlimiting example, the number of adjacent 2-D CT images may be three.

Training circuitry 116 may be further configured to capture output 105 that corresponds to training input image data 117. The output 105 may be generated by NN 114 based, at least in part, on input data 126 and based, at least in part, on current weights 124. Training circuitry 116 may be further configured to evaluate and/or optimize objective function (e.g., adversarial loss function 130 and/or perceptual loss function 132) based, at least in part, on output 105 and based, at least in part, on training output image data (i.e., one or more target output images) that corresponds to training input image data 117. Training circuitry 116 may be further configured to adjust at least one of a plurality of weights 124 based, at least in part, the evaluation of the adversarial loss function 130 and the perceptual loss function 132 associated with objective function circuitry 120.

In an embodiment, training circuitry 116 may be configured to train NN 114, i.e., adjust at least one 2-D weight of the plurality of weights 124, based, at least in part, on the objective function 120 and based, at least in part, on the 2-D training data. Training circuitry 116 may then be configured to provide 3-D training input data to the NN 114 and to refine the NN 114 by adjusting at least one of a plurality of 3-D weights based, at least in part, on the plurality of 2-D weights and based, at least in part, on the objective function. The plurality of 2-D weights includes the at least one adjusted 2-D weight.

In an embodiment, the NN 114 may be trained in a generative adversarial network (GAN) framework. In this example, the NN 114 may correspond to a generator of a GAN and training circuitry 116 may include a discriminator network, D network 122. In one nonlimiting example, the GAN may correspond to a Wasserstein GAN with gradient penalty.

Generally, a GAN includes a pair of neural networks (G, D), where G and D correspond to a generator and a discriminator, respectively. The generator, G, is configured to receive noise, z, as input and to generate samples, e.g., G(z), as output. The discriminator, D, is configured to receive the samples from the generator, G, and training data, x. The discriminator D is to distinguish between the generated samples G(z) and the training data, x. The two networks G, D, play a game, where the generator, G, is configured to learn to produce more and more realistic samples, and the discriminator is configured to learn to distinguish between synthesized data and real data. The two networks G, D are configured to be trained simultaneously with competition driving the generated samples to be indistinguishable from real data. Mathematically, the iterative optimization may be described by an objective function as:

$$\min_{\theta_G} \max_{\theta_D} E_{x \sim P_x}[\log D(x)] + E_{z \sim P_z}[\log(1 - D(G(z)))] \quad (1)$$

where $\theta_G$ and $\theta_D$ are the parameters of G and D, respectively, x is a real sample drawn from an unknown distribution $P_x$, and z is a noise input drawn from unknown distribution $P_z$.

A Wasserstein GAN (WGAN) is one variant of a GAN. In a WGAN, the discriminator lies within the space of 1-Lipschitz functions through weight clipping. In a variant of WGAN, the weight clipping may be replaced with a gradient penalty ("WGAN with gradient penalty"). A conditional GAN may be configured to produce new samples by providing label information. Based on a conditional GAN, an image may be transformed from one domain to another. For example, transforming from one domain to another may correspond to correcting images from LDCT to NDCT, according to the present disclosure.

Thus, during training NN 114 may correspond to a generative network and D network 122 may correspond to a discriminator network of a GAN. The GAN may correspond to a Wasserstein GAN with gradient penalty. The GAN may be based on conditional GANs. The trained NN may then be configured to correct an LDCT image to approximate a corresponding NDCT image. The correcting may include, for example, denoising (i.e., noise reduction) and/or artifact reduction.

An LDCT image may be represented as $I_{LD} \in \mathbb{R}^{w \times h}$ (i.e., a 2-D image) and a corresponding NDCT image mage be represented as $I_{ND} \in \mathbb{R}^{w \times h}$. A relationship between the LDCT image and the corresponding NDCT image may be represented as $$I_{LD} = \mathcal{N}(I_{ND}) \tag{2}$$

where $\mathcal{N}: \mathbb{R}^{w \times h} \to \mathbb{R}^{w \times h}$ represents a corrupting process due to quantum noise that contaminates the NDCT image. In other words, an LDCT image may include noise not present in a corresponding NDCT image. Approximating (e.g., denoising) a NDCT image based, at least in part, on a LDCT image corresponds to providing an approximate inverse $G \approx \mathcal{N}^{-1}$, estimating $I_{ND}$ from $I_{LD}$ as:

$$G(I_{LD}) = I_{est} \approx I_{ND} \tag{3}$$

As described herein, an objective function utilized for training a NN, e.g., NN 114, may include two loss functions: an adversarial loss function and a perceptual loss function, e.g., adversarial loss function 130 and perceptual loss function 132. A Wasserstein distance with gradient penalty for the adversarial loss function may be defined as:

$$\mathcal{L}_a = \mathbb{E}[D(I_{est})] - \mathbb{E}[D(I_{ND})] + \lambda \mathbb{E}[(\|\nabla D(\tilde{I})\|_2 - 1)^2] \tag{4}$$

where $\tilde{I}$ is uniformly sampled along straight lines between pairs of points sampled from the generated $I_{est}$ and the corresponding NDCT $I_{ND}$, and $\nabla$ denotes the gradient of D with respect to variable $\tilde{I}$. $\lambda$ is a weight parameter representing the trade-off between the Wasserstein distance term and the gradient penalty term.

In one nonlimiting example, the discriminator D (e.g., D network 122) has six convolutional layers, with 64, 64, 128, 128, 256 and 256 filter response maps, followed by two fully connected layers of size 1024 and 1. Each layer is followed by a leaky rectified linear unit (ReLU). A 3×3 filter is used for all convolutional layers. A unit filter stride is used for odd convolutional layers and this stride is doubled for even layers.

For the perceptual loss function, a perceptual similarity measure is configured to determine a distance between $I_{est}$ and $I_{ND}$ in a feature space by a differential function $\phi$ (feature map $\phi$), rather than in the image space. The perceptual loss function is configured to allow producing output images that may not match the NDCT image with pixel-wise accuracy, but drive the NN to generate images that have a visually relatively desirable feature representation. Such visually relatively desirable feature representation may optimally aid radiologists.

In one nonlimiting example, a pre-trained VGG-19 network may be utilized as the feature map $\phi$. VGG-19 is a 19 layer convolutional network that includes 16 convolutional layers and 3 fully-connected layers. VGG-19 uses 3×3 filters with stride and pad of 1 along with 2×2 max-pooling layers with stride 2. The feature map $\phi$ corresponds to the first 16 convolutional layers in the VGG network. The perceptual loss may then be defined as:

$$\mathcal{L}_p = \|\phi(I_{est}) - \phi(I_{ND})\|_2^2 \tag{5}$$

The objective function may then be defined as:

$$\mathcal{L} = \mathcal{L}_a + \lambda_p \mathcal{L}_p \tag{6}$$

where $\mathcal{L}_a$ corresponds to adversarial loss, $\mathcal{L}_p$ corresponds to perceptual loss and $\lambda_p$ is a weight. Inclusion of the perceptual loss term, $\mathcal{L}_p$, in the objective function is configured to encourage similarity between generated images and NDCT images in the feature space. Inclusion of the adversarial loss is configured to enhance textural information in approximated NDCT images (i.e., LDCT images with reduced noise and/or artifact(s)).

It may be appreciated that adjacent image slices (i.e., adjacent CT images) in a CT volume may have correlative features that can potentially improve 2-D-based noise reduction. Such spatial synergy may be used in radiologists' image reading when they step through a stack of 2-D images slices or view a plurality of image slices through volumetric rendering.

Since spatial correlation is generally strongest between adjacent LDCT slices, a single 2-D input image may be enhanced to include corresponding adjacent two slices, for example, upper and lower 2-D LDCT image slices. With an expanded input of three adjacent LDCT slices, a 2-D filter may be expanded to a 3-D filter. In one nonlimiting example, one 2-D input image may be augmented with three adjacent LDCT images. A 2-D w x h filter may then be replaced by a 3-D w×h×d filter.

Learned parameters of a 2-D filter (learned based on 2-D training data) may be extended to a corresponding 3-D filter. The correspond in 3-D filter may then be refined based, at least in part, on 3-D training data. In one nonlimiting example, $H \in \mathbb{R}^{3 \times 3}$ may correspond to a trained 2-D filter. A corresponding 3-D filter, $B \in \mathbb{R}^{3 \times 3 \times 3}$, may then be initialized as:

$$B_{(0)} = 0_{3 \times 3}, B_{(1)} = H_{3 \times 3}, B_{(2)} = 0_{3 \times 3} \tag{7}$$

where each subscript of B corresponds to a respective LDCT image slice of a plurality of adjacent image slices. A resultant 3-D NN may then provide a similar performance to the corresponding 2-D trained NN. The resultant 3-D convolutional network may then be trained to improve its performance (i.e., refined) based, at least in part, on the adjacent image slices.

Thus, NN 114 may be initially trained based, at least in part, on 2-D training image pairs by adjusting at least one 2-D weight of the plurality of weights 124. The NN 114 may then be refined based, at least in part, on 3-D training image pairs by adjusting the plurality of weights 124 that includes the at least one adjusted 2-D weight. Training then refining the NN 114 may be relatively less computationally expensive than directly training the NN 114 using 3-D input data.

Figure 2:
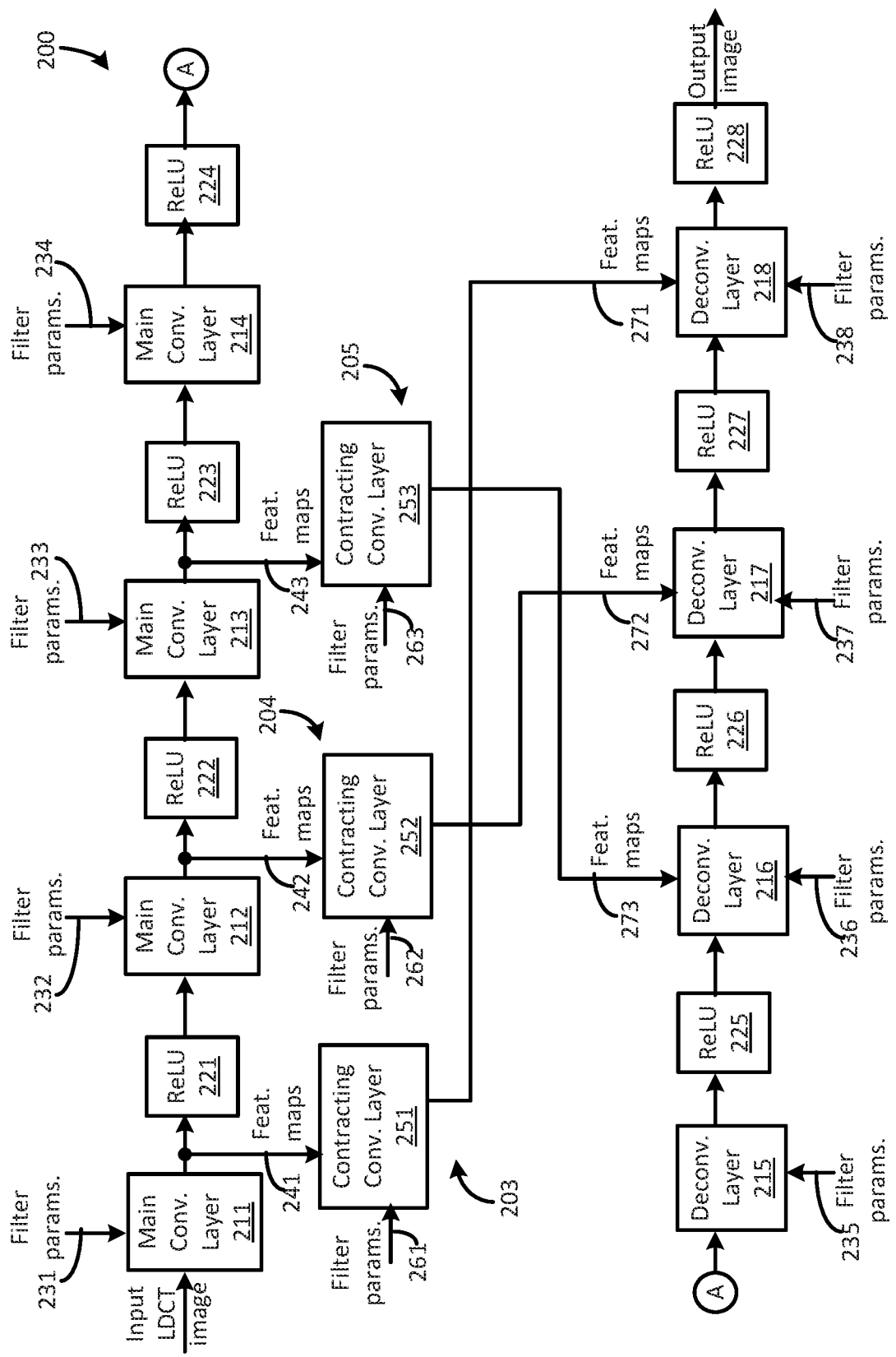
FIG. 2 illustrates a functional block diagram of one example neural network according to the present disclosure.

FIG. 2 illustrates a functional block diagram of one example NN 200 according to the present disclosure. NN 200 is one example of NN 114 of FIG. 1. NN 200 is configured to receive an input image, for example, an LDCT image that may include noise and/or artifacts and to provide as output a corrected output image that approximates a corresponding NDCT image. In other words, the approximated NDCT image may include relatively less noise and/or relatively fewer artifacts compared to the LDCT input image. In one nonlimiting example, NN 200 may correspond to a convolutional neural network (CNN). In another nonlimiting example, NN 200 may correspond to a contracting path-based convolutional autoencoder (CPCA), as described herein.

Generally, NN 200 includes a plurality of main convolutional layers coupled in series, a plurality of deconvolutional layers coupled in series and a plurality of contracting paths, with each contracting path coupled between an output of a respective convolutional layer and a respective selected deconvolutional layer. NN 200 may further include a plurality of rectified linear units ("ReLUs") with each ReLU coupled to an output of a respective main convolutional layer or an output of a deconvolutional layer. In this example, NN 200 includes four main convolutional layers, four deconvolutional layers and three contracting paths, however, this disclosure is not limited in this regard.

NN 200 includes a first main convolutional layer 211, a second main convolutional layer 212, a third main convolutional layer 213 and a fourth main convolutional layer 214. NN 200 includes a first main deconvolutional layer 215, a second main deconvolutional layer 216, a third main deconvolutional layer 217 and a fourth main deconvolutional layer 218. NN 200 further includes a first contracting path 203 coupled between an output of the first main convolutional layer 211 and the fourth deconvolutional layer 218; a second contracting path 204 coupled between an output of the second main convolutional layer 214 and the third deconvolutional layer 217 and a third contracting path 205 coupled between an output of the third main convolutional layer 213 and the second deconvolutional layer 216.

An output of each main convolutional layer 211, 212, 213, 214 and an output of each main deconvolutional layer 215, 216, 217, 218 is coupled to a respective ReLU 221, 222, . . . , 228, respectively. Each main convolutional layer 211, 212, 213, 214 and each main deconvolutional layer 215, 216, 217, 218 is configured to receive respective filter parameters 231, 232, . . . , 238, respectively. An output of each ReLU 221, 222, 223 is coupled to an input of a respective subsequent main convolutional layer 212, 213, 214 and an output of each ReLU 225, 226, 227 is coupled to an input of a respective subsequent main deconvolutional layer 216, 217, 218. An output of ReLU 224 is connected to an input of the first deconvolutional layer 215 (indicated by "A" in FIG. 2) and an output of ReLU 228 corresponds to an output of NN 200, i.e., the output image (approximated NDCT image that corresponds to the LDCT input image).

Each contracting path 203, 204, 205 includes a respective contracting convolutional layer 251, 252, 253, respectively. Each contracting convolutional layer 251, 252, 253 is configured to receive a respective filter parameters 261, 262, 263 and a respective feature map 241, 242, 243 from a respective main convolutional layer 211, 212, 213. Each contracting convolutional layer 251, 252, 253 is configured to provide a respective feature map 271, 272, 273 to a respective main deconvolutional layer 218, 217, 216. The respective feature maps are configured to facilitate deconvolution operations of deconvolution layers 216, 217, 218.

During training of NN 200, training circuitry 116 of FIG. 1 is configured to adjust filter parameters 231, 232, . . . , 238, 261, 262, 263 based, at least in part, on training input image data, a corresponding target output image and objective function 120. Initially, training input image data may correspond to a 2-D training input image, i.e., one slice, and the 2-D filter parameters 231, 232, . . . , 238, 261, 262, 263 may have a depth of one.

The convolutional network 200 may then be refined based, at least in part, on 3-D training data. The 3-D training data may include a plurality of 3-D training image pairs. Each 3-D training image pair may include a plurality of adjacent training input images (i.e., a plurality of adjacent slices) and at least one corresponding target output image. Training circuitry 116 may be configured to adjust at least one of a plurality of 3-D filter parameters based, at least in part, on the plurality of 2-D filter parameters and based, at least in part, on the objective function. The plurality of 2-D filter parameters includes the at least one adjusted 2-D filter parameter. The 3-D filter parameters 231, 232, . . . , 238, 261, 262, 263 may have a depth greater than one. In one non-limiting example, the 3-D filter parameters may have a depth of three (e.g., depths d1, d2, d3 corresponding to subscripts (0), (1), (2), respectively, in Eq. (7)). Continuing with this example, initially, prior to refining (and following the initial training), the 3-D filter parameter layer corresponding to depth d2 may be set to the corresponding 2-D filter parameter values and the 3-D filter parameter layers corresponding to the depths d1 and d3 may be initialized to zero. Thus, 2-D learning may be utilized to facilitate 3-D learning and may thus be relatively more computationally efficient compared to 3-D learning started from scratch.

Thus, during training, initially, NN 200 is configured to receive 2-D input images individually and filter parameters may be correspondingly 2-D. During refining, NN 200 is configured to receive 3-D input image data and filter parameters may be 3-D. At the start of refining, the 3-D filter parameters may include a middle depth layer initialized with the corresponding 2-D filter values. Thus, training the 3-D NN may benefit from the prior 2-D training.

During normal operation, the first main convolutional layer 211 is configured to receive an input image (2-D) or a plurality of input images (3-D) and, after processing, ReLU 228 is configured to provide as output a rectified output of the fourth main deconvolutional layer 218. The rectified output of the fourth main deconvolutional layer 218 may then correspond to an approximated NDCT image. The approximated NDCT image corresponds to the input LDCT image with noise and/or artifacts reduced.

Figure 3:
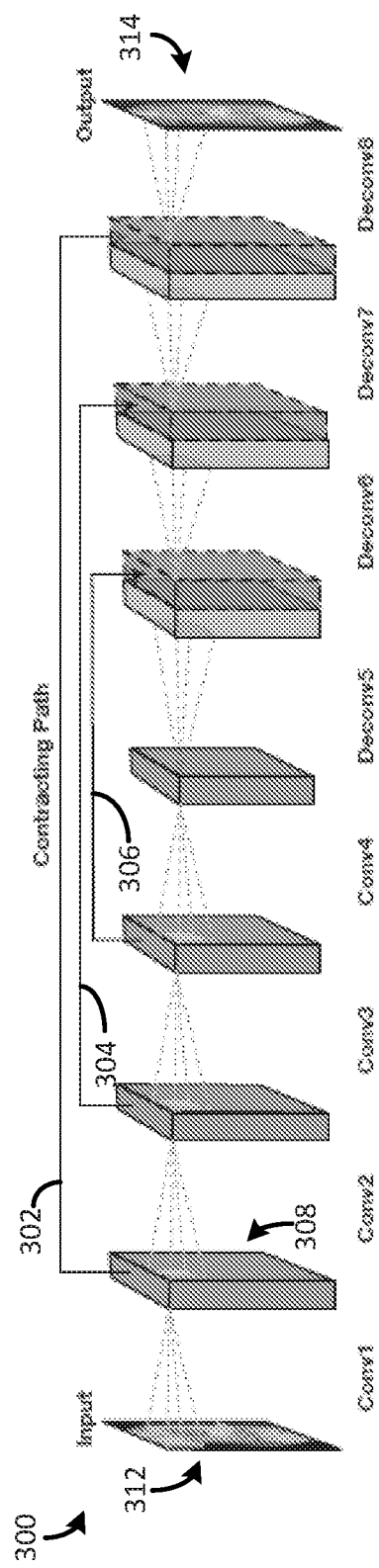
FIG. 3 is a sketch illustrating operations of one example NN consistent with one embodiment of the present disclosure.

FIG. 3 is a sketch illustrating operations of one example NN 300 consistent with one embodiment of the present disclosure. Example 300 includes four convolutional layers Conv1, . . . , Conv4 followed by four deconvolutional layers Deconv5, . . . , Deconv8. Example 300 further includes three contracting paths 302, 304, 306. In this example, each convolutional layer and each deconvolutional layer has fixed 32 filter response maps. Each filter is 3×3 with a filter stride of 1. The contracting paths are configured to copy feature maps from the convolutional layers and reuse the copied feature maps in the later deconvolutional layers. For example, contracting path 302 is configured to copy feature map 308 that is the output of convolutional layer Conv1 to deconvolutional layer Deconv7. Copying the feature maps is configured to preserve details of high resolution features. In order to reduce computational cost, each contracting path may be followed by a respective convolutional layer with 1×1 filter configured to reduce the number of feature maps from 64 to 32. Each convolutional layer and each deconvolutional layer may be followed by a respective ReLU. Conv1 is configured to receive an input image 312, corresponding to a 2-D LDCT image. Deconv8 is configured to provide as output a corrected image 314 approximating an NDCT image corresponding to input image 312, as described herein.

Figure 4:
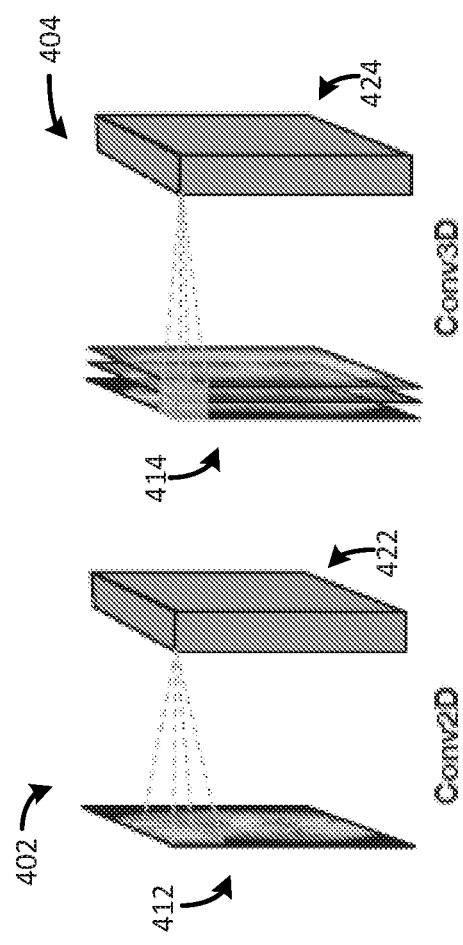
FIG. 4 is a sketch illustrating transfer learning from a two-dimensional NN to a three-dimensional NN consistent with one embodiment of the present disclosure.

FIG. 4 is a sketch illustrating transfer learning from a 2-D NN 402 to a 3-D NN 404 consistent with one embodiment of the present disclosure. The 2-D NN 402 includes one convolutional layer Conv2D configured to receive a 2-D input image 412 and to provide as output a feature map 422. The 3-D NN 404 includes one convolutional layer Conv3D configured to receive a 3-D input 414 that includes three 2-D images. The 3-D convolutional layer Conv3D is configured to provide as output a feature map 424. The 2-D NN Conv2D corresponds to a 2-D filter, e.g., 3×3 and the 3-D NN Conv3D corresponds to a 3-D filter, e.g., 3×3×3. The resulting feature maps 422, 424 may have a same size.

Figure 5:
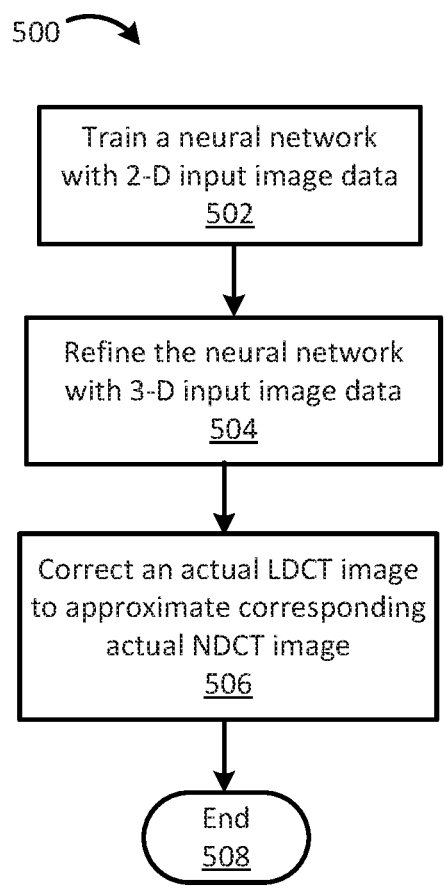
FIG. 5 is a flowchart of example neural network operations consistent with several embodiments of the present disclosure.

FIG. 5 is a flowchart 500 of example NN operations consistent with several embodiments of the present disclosure. In particular, flowchart 500 illustrates training a NN then correcting an LDCT image using the trained NN. The operations of flowchart 500 may be performed by, for example, correction circuitry 104 (e.g., NN 114, training circuitry 116 and/or objective function circuitry 120) of FIG. 1.

Operations of flowchart 500 may begin with training a NN with 2-D input image data. The training may include adjusting at least one of a plurality of 2-D weights, as described herein. The NN may then be refined at operation 502. The refining may include adjusting at least one of a plurality of 3-D weights based, at least in part, on the plurality of 2-D weights including the at least one adjusted 2-D weight. Operation 506 may include correcting, by the trained NN, an actual LDCT image to approximate a corresponding actual normal dose CT (NDCT) image. The correcting may include at least one of noise reduction and/or artifact reduction.

Thus, a NN may be initially trained using 2-D input images and refined using 3-D image data.

Example

FIGS. 6 through 10 illustrate experimental data from an actual clinical low dose CT data set. The images were taken from 10 anonymous patients and include normal those abdominal CT images and simulated quarter dose CT images. The slice thickness and reconstruction interval in this data set were 1.0 millimeters (mm) and 0.8 mm, respectively. For training purposes, the low dose images of five patients, which contain 128,000 image patches of size 64×64, were selected from this data set. To test the performance of the trained NN, 64,000 randomly selected image patches were taken from five different patients. Adjacent low dose image patches were maintained for training and testing.

During training, an Adam optimization technique was used to train the NN using disjoint subsets of 128 patches for each iteration. In the training phase, the learning rate was selected to be $1.0 \times 10^{-4}$ with two exponential decay rates $\beta_1=0.9$ and $\beta_2=0.999$ for the moment estimates. The learning rate was halved for training based on transfer learning, which was followed by refining (i.e., fine tuning). The learning rate was adjusted by 1/t decay; namely, $\alpha_t=\alpha/t$ at the $t^{th}$ epoch. The parameter $\lambda$ for the trade-off between the Wasserstein distance and gradient penalty was set to be 10. The parameter $\lambda_p$ for the perceptual loss in the objective function was set to 0.1.

Figure 6:
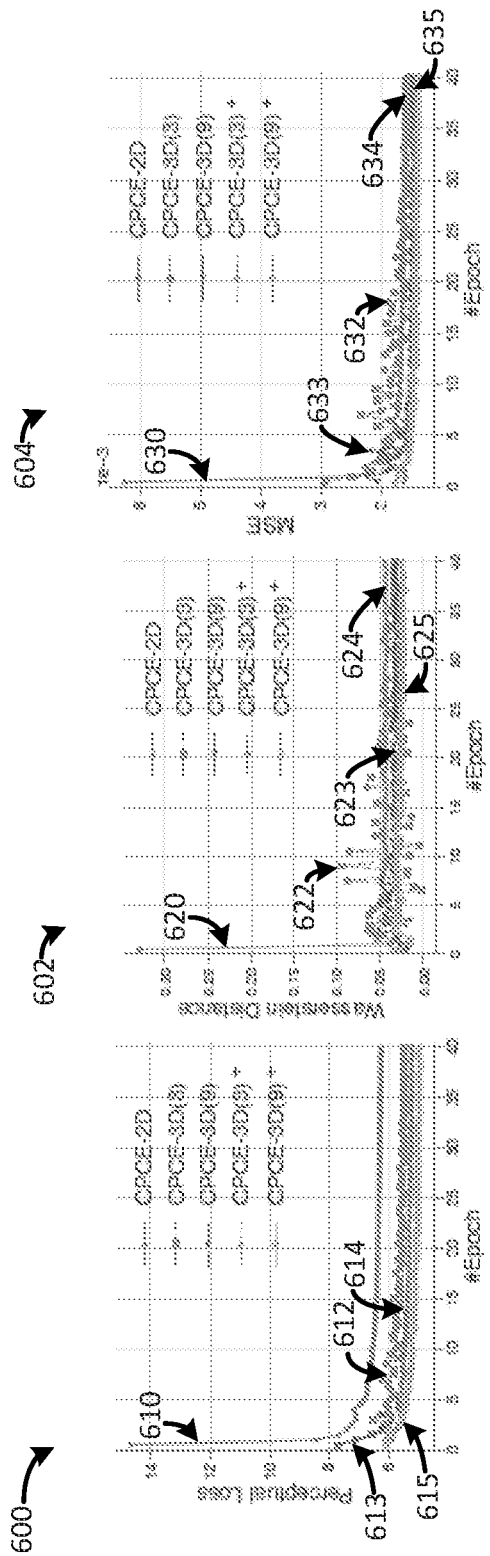
FIG. 6 includes plots illustrating convergence of perceptual loss, Wasserstein distance and MSE (mean squared error) loss functions, respectively.

FIG. 6 includes plots illustrating convergence of perceptual loss 600, Wasserstein distance 602 and MSE (mean squared error) 604 loss functions, respectively. The horizontal axis of plots 600, 602 and 604 correspond to number of epochs with loss determined at each one half epoch. Plot 600 includes perceptual loss convergence for 2-D CPCE 610; 3-D CPCE with three input slices, from scratch 612; 3-D CPCE with nine input slices, from scratch 613; 2-D to 3-D CPCE with three input slices 614 and 2-D to 3-D CPCE with nine input slices 615. Plot 602 includes Wasserstein distance convergence for 2-D CPCE 620; 3-D CPCE with three input slices, from scratch 622; 3-D CPCE with nine input slices, from scratch 623; 2-D to 3-D CPCE with three input slices 624 and 2-D to 3-D CPCE with nine input slices 625. Plot 604 includes MSE (mean squared error) convergence for 2-D CPCE 630; 3-D CPCE with three input slices, from scratch 632; 3-D CPCE with nine input slices, from scratch 633; 2-D to 3-D CPCE with three input slices 634 and 2-D to 3-D CPCE with nine input slices 635.

Figure 7:
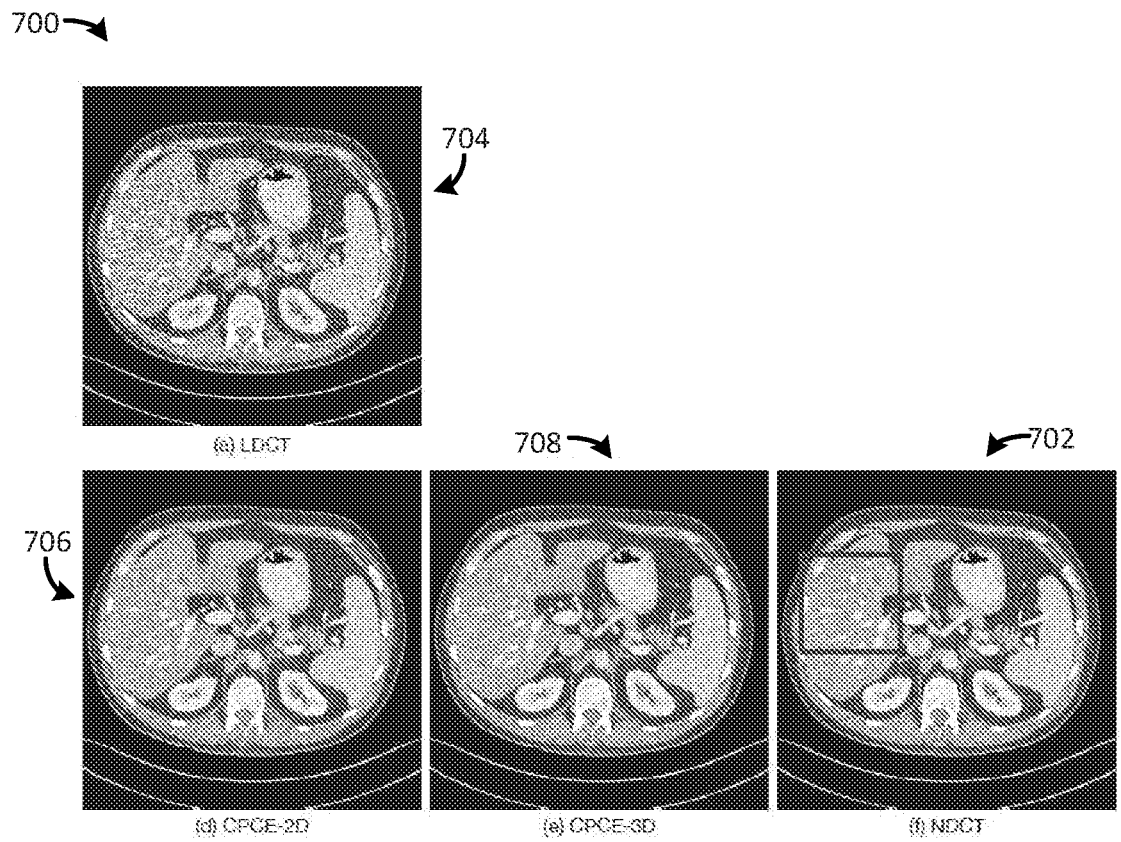
FIG. 7 illustrates example transverse CT images of a first slice of an abdomen.

FIG. 7 illustrates example 700 transverse CT images of a first slice of an abdomen. Image 702 is a normal dose CT image of the first slice. Image 704 is a low dose CT image of the first slice. Image 706 corresponds to an output of a 2-D CPCE, consistent with the present disclosure, with the low dose image of the first slice as input. Image 708 corresponds to an output of a 3-D CPCE, consistent with the present disclosure, with the low dose image of the first slice and adjacent images as input.

Figure 8:
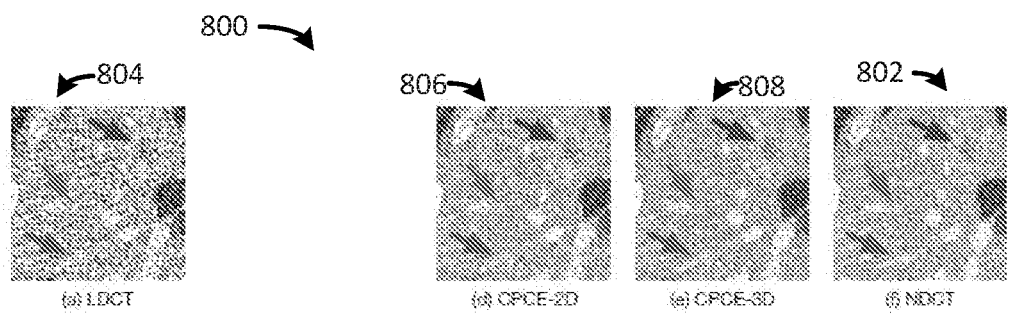
FIG. 8 illustrates a zoomed in portion of example transverse CT images of FIG. 7.

FIG. 8 illustrates a zoomed in portion 800 of example transverse CT images of FIG. 7. Image 802 is a normal dose CT image of a zoomed in portion of the first slice. Image 804 is a low dose CT image of the zoomed in portion of the first slice. Image 806 corresponds to an output of a 2-D CPCE, consistent with the present disclosure, with the low dose image of the first slice as input. Image 808 corresponds to an output of a 3-D CPCE, consistent with the present disclosure, with the low dose image of the first slice and adjacent images as input.

Figure 9:
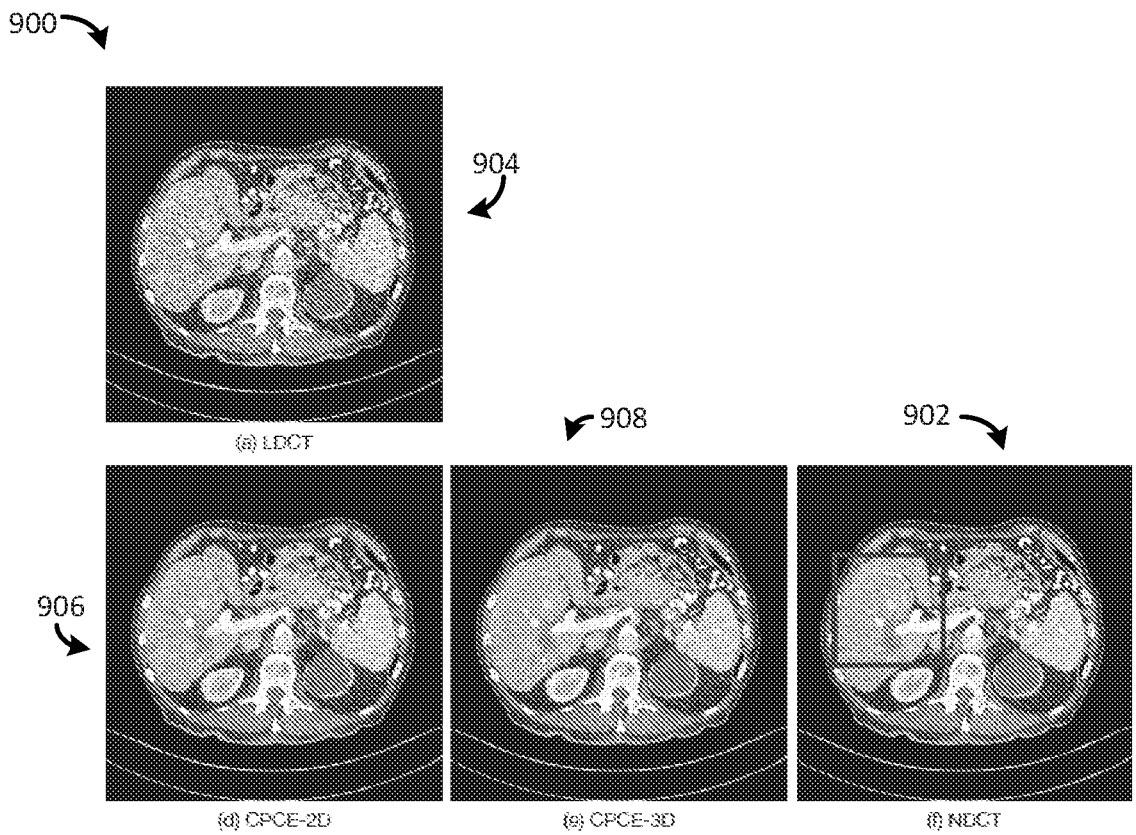
FIG. 9 illustrates example transverse CT images of a second slice of an abdomen.

FIG. 9 illustrates example 900 transverse CT images of a second slice of an abdomen. Image 902 is a normal dose CT image of the second slice. Image 904 is a low dose CT image of the second slice. Image 906 corresponds to an output of a 2-D CPCE, consistent with the present disclosure, with the low dose image of the second slice as input. Image 908 corresponds to an output of a 3-D CPCE, consistent with the present disclosure, with the low dose image of the second slice and adjacent images as input.

Figure 10:
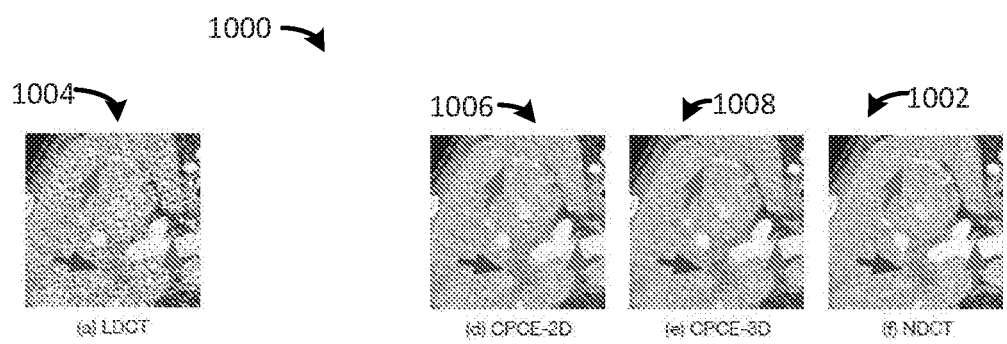
FIG. 10 illustrates a zoomed in portion of example transverse CT images of FIG. 9.

FIG. 10 illustrates a zoomed in portion 1000 of example transverse CT images of FIG. 9. Image 1002 is a normal dose CT image of a zoomed in portion of the second slice. Image 1004 is a low dose CT image of the zoomed in portion of the second slice. Image 1006 corresponds to an output of a 2-D CPCE, consistent with the present disclosure, with the low dose image of the second slice as input. Image 1008 corresponds to an output of a 3-D CPCE, consistent with the present disclosure, with the low dose image of the second slice and adjacent images as input.

Thus, a method, system and/or apparatus is configured to train the NN using 2-D CT image data. The training includes determining 2-D weights to optimize the objective function. The method, system and/or apparatus is then configured to fine tune (i.e., refine) the NN using 3-D image data and based, at least in part, on the 2-D weights. Training the NN using 2-D image data and refining based, at least in part, on the 2-D weights is generally less computationally expensive than training from scratch using 3-D image data.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hard-wired circuitry, programmable circuitry such as computer processors including one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a field-programmable gate array (FPGA), a programmable logic device (PLD), a complex programmable logic device (CPLD), a system on-chip (SoC), etc.

Memory 112 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively memory 112 may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

What is claimed is:

1. A method for low dose computed tomography (LDCT) image correction, the method comprising:
   training, by a training circuitry, a convolutional neural network (CNN) based, at least in part, on two-dimensional (2-D) training data, the 2-D training data comprising a plurality of 2-D training image pairs, each 2-D image pair comprising one training input image and one corresponding training output image, the training comprising adjusting at least one of a plurality of 2-D filter parameters based, at least in part, on an objective function; and;
   refining, by the training circuitry, the CNN based, at least in part, on three-dimensional (3-D) training data, the 3-D training data comprising a plurality of 3-D training image pairs, each 3-D training image pair comprising a plurality of adjacent 2-D training input images and at least one corresponding training output image, the refining comprising adjusting at least one of a plurality of 3-D filter parameters based, at least in part, on the plurality of 2-D filter parameters and based, at least in part, on the objective function, the plurality of 2-D filter parameters comprising the at least one adjusted 2-D filter parameter;
   wherein the CNN is a contracting path-based convolutional auto encoder (CPCA) comprising a plurality of main convolutional layers, a plurality of deconvolutional layers and a plurality of contracting paths, each contracting path coupled between an output of a respective convolutional layer and a respective selected deconvolutional layer, each of the plurality of contracting paths comprises a respective contracting convolutional layer configured to receive as input a respective first feature map from a respective selected main convolutional layer and to output a respective second feature map to a respective selected deconvolutional layer, the respective second feature map being different than the respective first feature map.

2. The method of claim 1, wherein the CNN corresponds to a generator network of a Wasserstein generative adversarial network (WGAN) with gradient penalty.

3. The method of claim 1, wherein the objective function comprises an adversarial loss function and a perceptual loss function.

4. The method of claim 1, wherein each 3-D training image pair comprises three adjacent 2-D training input images.

5. The method of claim 1, wherein the image correction corresponds to denoising an LDCT image to approximate a corresponding normal dose CT (NDCT) image.

6. The method of claim 1, further comprising correcting, by the trained CNN, an actual LDCT image to approximate a corresponding actual normal dose CT (NDCT) image, the correcting comprising at least one of noise reduction and/or artifact reduction.

7. A convolutional neural network (CNN) stored on a non-transitory computer readable storage medium and configured to be executed by one or more processors of the non-transitory computer readable storage medium, the CNN comprising:
   a contracting path-based convolutional auto encoder (CPCA) comprising:
      a plurality of main convolutional layers coupled in series;
      a plurality of deconvolutional layers coupled in series; and
      a plurality of contracting paths, each contracting path coupled between an output of a respective convolutional layer and a respective selected deconvolutional layer, each of the plurality of contracting paths comprises a respective contracting convolutional layer configured to receive as input a respective first feature map from a respective selected main convolutional layer and to output a respective second feature map to a respective selected deconvolutional layer, the respective second feature map being different than the respective first feature map;
   wherein the CPCA is trained based, at least in part, on two-dimensional (2-D) training data, the 2-D training data comprising a plurality of 2-D training image pairs, each 2-D image pair comprising one training input image and one corresponding training output image, the training comprising adjusting at least one of a plurality of 2-D filter parameters based, at least in part, on an objective function and the CPCA is refined based, at least in part, on three-dimensional (3-D) training data, the 3-D training data comprising a plurality of 3-D training image pairs, each 3-D training image pair comprising a plurality of adjacent 2-D training input images and at least one corresponding training output image, the refining comprising adjusting at least one of a plurality of 3-D filter parameters based, at least in part, on the plurality of 2-D filter parameters and based, at least in part, on the objective function, the plurality of 2-D filter parameters comprising the at least one adjusted 2-D filter parameter.

8. The CNN of claim 7, wherein the CPCA corresponds to a generator network of a Wasserstein generative adversarial network (WGAN) with gradient penalty.

9. The CNN of claim 7, wherein the objective function comprises an adversarial loss function and a perceptual loss function.

10. The CNN of claim 7, wherein the CPCA is configured to correct an actual low dose computed tomography (LDCT) image to approximate a corresponding actual normal dose computed tomography (NDCT) image, the correcting comprising at least one of noise reduction and/or artifact reduction.

11. The CNN according to claim 7, wherein the CPCA comprises a first main convolutional layer, a second main convolutional layer, a third main convolutional layer and a fourth main convolutional layer; a first deconvolutional layer, a second deconvolutional layer, a third deconvolutional layer and a fourth deconvolutional layer; and a first contracting path coupling an output of the first main convolutional layer to the fourth deconvolutional layer, a second contracting path coupling an output of the second main convolutional layer to the third deconvolutional layer, and a third contracting path coupling an output of the third main convolutional layer to the second deconvolutional layer.

12. The CNN according to claim 7, further comprising a plurality of rectified linear units (ReLUs), each ReLU coupled an output of a respective main convolutional layer or an output of a respective deconvolutional layer.

13. A low dose computed tomography (LDCT) image correction system comprising at least one device arranged to perform the method of claim 1.

14. A low dose computed tomography (LDCT) image correction device comprising means to perform the method of claim 1.

15. A computer readable storage device having stored thereon instructions that when executed by one or more processors result in the following operations comprising the method according to claim 1.

* * * * *